US011040090B2

United States Patent
Singh

(10) Patent No.: US 11,040,090 B2
(45) Date of Patent: Jun. 22, 2021

(54) BOTULINUM NEUROTOXIN COMPOSITIONS

(71) Applicant: Bal Ram Singh, Dartmouth, MA (US)

(72) Inventor: Bal Ram Singh, Dartmouth, MA (US)

(73) Assignee: Prime Bio, Inc, North Dartmouth, MA (US)

( * ) Notice: Subject to any disclaimer, the term of this patent is extended or adjusted under 35 U.S.C. 154(b) by 0 days.

(21) Appl. No.: 15/372,560

(22) Filed: Dec. 8, 2016

(65) Prior Publication Data

US 2018/0161406 A1 Jun. 14, 2018

(51) Int. Cl.
| | |
|---|---|
| *A61K 38/48* | (2006.01) |
| *C12N 15/09* | (2006.01) |
| *C12N 9/64* | (2006.01) |
| *C12N 9/52* | (2006.01) |
| *A61K 9/00* | (2006.01) |
| *A61K 31/165* | (2006.01) |
| *A61K 47/02* | (2006.01) |
| *A61K 47/55* | (2017.01) |
| *A61K 45/06* | (2006.01) |

(52) U.S. Cl.
CPC ........ *A61K 38/4893* (2013.01); *A61K 9/0019* (2013.01); *A61K 31/165* (2013.01); *A61K 45/06* (2013.01); *A61K 47/02* (2013.01); *A61K 47/55* (2017.08); *C12N 9/52* (2013.01); *C12N 9/6489* (2013.01); *C12N 15/09* (2013.01); *C12Y 304/24069* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 6,699,966 | B1 * | 3/2004 | Singh | C07K 14/33 530/350 |
| 6,994,859 | B1 * | 2/2006 | Singh | A61K 39/08 424/247.1 |
| 7,431,935 | B2 * | 10/2008 | Singh | C07K 14/33 424/239.1 |
| 7,744,904 | B1 * | 6/2010 | Singh | C12Y 304/24069 424/236.1 |
| 7,981,432 | B2 * | 7/2011 | Singh | C07K 14/33 424/239.1 |
| 8,586,081 | B2 * | 11/2013 | Singh | A61K 39/08 424/450 |
| 8,748,106 | B2 | 6/2014 | Singh | |
| 9,139,624 | B2 * | 9/2015 | Singh | A61K 39/08 |
| 9,526,827 | B2 * | 12/2016 | Fischell | A61M 5/158 |
| 2006/0198883 | A1 * | 9/2006 | Parks | A61K 9/0031 424/451 |
| 2009/0053290 | A1 * | 2/2009 | Sand | A61K 8/34 424/449 |
| 2010/0222254 | A1 | 9/2010 | Singh | |
| 2012/0171247 | A1 * | 7/2012 | Singh | C07K 14/33 424/239.1 |
| 2012/0302507 | A1 * | 11/2012 | Ham | A61K 38/4893 514/18.1 |
| 2017/0290778 | A1 * | 10/2017 | Waugh | A61K 9/7023 |
| 2018/0161406 | A1 * | 6/2018 | Singh | A61K 38/4893 |
| 2019/0008795 | A1 * | 1/2019 | Waugh | A61K 47/36 |
| 2019/0076518 | A1 * | 3/2019 | Singh | A61K 39/099 |
| 2019/0136216 | A1 * | 5/2019 | Dong | C07K 14/33 |
| 2019/0201506 | A1 * | 7/2019 | Lee | A61K 47/18 |

FOREIGN PATENT DOCUMENTS

| | | | | |
|---|---|---|---|---|
| WO | WO-2007038282 A2 * | 4/2007 | ........... | C12N 9/6416 |
| WO | WO-2007103555 A2 * | 9/2007 | ............. | A61K 8/553 |
| WO | WO-2018009903 A2 * | 1/2018 | ............... | C12N 9/52 |
| WO | WO-2018038585 A1 * | 3/2018 | ............. | A61K 47/08 |

OTHER PUBLICATIONS

Singh et alJ Protein Chemistry, 1990, 9/6:705-713 (Year: 1990).*
Byrant et al, Toxicon, 2013, 72:126-132. available online: Jun. 28, 2013 (Year: 2013).*
Carruthers et al, Dermatologic Surgery, Dec. 2005, 31:1655-1659 (Year: 2005).*
Perez et al BMC Neurology, 2010, 10:20. 14 pages published: Mar. 31, 2010 (Year: 2010).*
Pazin et al, Int. Urogynecol. J., 2016, 27:697-708. published online: Aug. 14, 2015 (Year: 2015).*
Goodnough et al, Applied and Environmental Microbiology, Oct. 1992, 58/10:3426-3428 (Year: 1992).*
Smith et al, Journal of Urology, 2004, 171:2128-2137. (Year: 2004).*
Carruthers et al, Dermatol. Surg., Dec. 2005, 31/12:1655-1659 (Year: 2005).*
Singh BR. Role of neurotoxin associated proteins in the low pH induced structural changes in the botulinum neurotoxin complex. Protein J. Dec. 2014;33(6):557-64. USA.
Singh BR. Comparative role of neurotoxin-associated proteins in the structural stability and endopeptidase activity of botulinum neurotoxin complex types A and E. Biochemistry. Dec. 11, 2007;46(49):14316-24. USA.

* cited by examiner

*Primary Examiner* — Nita M. Minnifield
(74) *Attorney, Agent, or Firm* — Carrie M. Stroup

(57) ABSTRACT

Present invention provides a stable pharmaceutical composition comprising botulinum neurotoxin, anesthetic in a buffer. Present invention also provides a process for the preparation of the stable pharmaceutical composition. The *botulinum* neurotoxin is stabilized by the formation of complex between the toxin and anesthetic. The present invention further provides a method for treating wrinkles using the said pharmaceutical composition.

22 Claims, 5 Drawing Sheets

BOTULINUM NEUROTOXIN COMPOSITIONS

FIELD OF THE INVENTION

Present invention relates a stable composition of *botulinum* neurotoxin with the help of a local anesthetic in a buffer. Present invention also relates a process for producing the said stable composition of botulinum neurotoxin and anesthetic in a buffer. The present invention provides a solution to degradation or denaturation of *botulinum* neurotoxin by providing stable *botulinum* neurotoxin in presence of an anesthetic in a buffer.

BACKGROUND OF THE INVENTION

The present invention relates to a pharmaceutical composition comprising *Clostridium botulinum* neurotoxin and to a method of stabilizing the same. The stabilization of neurotoxin achieved by the help of local anesthetic in a buffer. Particularly, the present invention is directed to a stabilized pharmaceutical composition including *C. botulinum* Type A neurotoxin and a local anesthetic.

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. *Botulinum* neurotoxins are produced from anaerobic bacillus *Clostridium botulinum*. Seven related protein neurotoxins, known as serotypes A through G, are produced by different strains of the bacillus. The molecular weight of the *botulinum* toxin protein molecule, for all seven of the known *botulinum* toxin serotypes, is about 150 kDa. Interestingly, the *botulinum* toxins are released by Clostridial bacterium as complexes comprising the 150 kDa *botulinum* toxin protein molecule along with associated non-toxin proteins. Thus, the *botulinum* toxin type A complex can be produced by Clostridial bacterium as 900 kDa, 500 kDa, and 300 kDa forms. Botulinum toxin types B and C1 is apparently produced as only a 700 kD or 500 kD complex. Botulinum toxin type D is produced as both 300 kD and 500 kD complexes. Finally, *botulinum* toxin types E and F are produced as only approximately 300 kD complexes, although larger complexes of these are known to exist. The complexes (i.e. molecular weight greater than about 150 kD) are believed to contain a group of non-toxin hemaglutinin proteins and a non-toxin and non-toxic non-hemaglutinin protein. These two groups of non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kDa molecular weight) *botulinum* toxin complexes may result in a slower rate of diffusion of the *botulinum* toxin away from a site of intramuscular injection of a *botulinum* toxin complex.

*Clostridium botulinum* neurotoxins, which cause the disease of botulism by blocking the release of the neurotransmitter, acetylcholine at the neuromuscular junction, are the most toxic proteins currently known to mankind. Food-borne botulism results from the consumption of improperly stored foods in which anaerobic *C. botulinum* grows and releases the toxin. In other forms of botulism, *C. botulinum* also produces the neurotoxin resulting in toxigenesis. For example, wound botulism results when the spores of *C. botulinum* are introduced into an open skin abrasion. The colonization of the wound is followed by the release of *botulinum* toxin. Similarly, infant botulism results from the consumption of *C. botulinum* spores followed by colonization in the intestine and toxigenesis. BoNTs are $Zn^{2+}$-endopeptidases (Schiavo, Benfenati et al. 1992, Blasi, Chapman et al. 1993) has led to the identification of several target proteins, which are critical for the docking and fusion of synaptic vesicles to the plasma membrane in the neurotransmitter release process. Cellubrevin, SNAP-25 (synaptosomal associated protein of 25 kDa), and syntaxin form the SNARE complex during docking of synaptic vesicles to the plasma membrane. Different BoNT types proteolytically cleave cellubrevin (BoNT/B, BoNT/C, BoNT/D, and BoNT/F), SNAP-25 (BoNT/A, BoNT/C, and BoNT/E), and syntaxin (BoNT/C) as part of their mode of action to block neurotransmitter release. Because of their specificity to inhibit neurotransmitter release at neuromuscular junctions, BoNT is increasingly being used to treat various neuromuscular disorders such as strabismus, torticollis, and blepherospasm (Johnson 1999).

Botulinum Neurotoxin (BoNT) produced by the bacterium *Clostridium botulinum* as a complex with several non-toxic neurotoxin-associated proteins (NAPs) causes botulism. It has been known that the NAPs protect the toxin from both extremes of pHs and proteases of the GI tract. NAPs protect the inherently fragile BoNTs against the hostile environment of the gastrointestinal (GI) tract and help BoNTs pass through the intestinal epithelial barrier before they are released into the general circulation. These events are essential for ingested BoNTs to gain access to motor-neurons, where they inhibit neurotransmitter release and cause muscle paralysis. It is proven that all serotypes of BoNT in its native stable and non-covalent complex with NAPS to form progenitor toxin complexes (PTCs). The NAPs protect BoNTs to reduce oral lethal dose by 10 to 100 folds compared to free BoNT.

Although the *botulinum* neurotoxins are known to be the most lethal natural toxin known to man, these lethal poisons have become utilized in the medical community as drugs with many indications. In this regard, the *botulinum* neurotoxins have been used to treat strabismus, and local injections of *botulinum* neurotoxin are now considered a safe and efficacious treatment for many neurological and non-neurological conditions. Recently, it has been observed that *botulinum* neurotoxin is useful as a treatment for diseases of the gastrointestinal tract. Botulinum neurotoxin is not only potent in blocking skeletal neuromuscular transmission, but also block cholinergic nerve endings in the autonomic nervous system. The capability to inhibit contraction of smooth muscles of the gastrointestinal tract was first suggested based on in vitro observations and later demonstrated in vivo, it has also been shown that *botulinum* neurotoxin does not block non adrenergic non cholinergic responses mediated by nitric oxide. This has further promoted the interest to use *botulinum* neurotoxin as a treatment for overactive smooth muscles and sphincters, such as the lower esophageal sphincter to treat esophageal achalasia, or the internal anal sphincter to treat anal fissure.

Commercially available pharmaceutical compositions comprising *botulinum* toxin are marketed under the trademarks including BOTOX™. (Allergan, Inc. Irvine Calif.), Dysport™. (Ipsen Ltd. Berkshire, U.K.), Xeomin™ (Frankfurt, Germany) and Myobloc™. (Elan Corp. Dublin Ireland). Typically, the pharmaceutical compositions are sold as vacuum-dried form that must be reconstituted with a diluent prior to actual usage. One major drawback to using the commercially available *botulinum* toxin preparations is the very short shelf life of the composition. In this regard, the actual usage of the pharmaceutical composition should be administered within about four hours after reconstitution because the *botulinum* toxin is very susceptible to denaturation due to surface denaturation, heat, and alkaline conditions.

The commercially available pharmaceutical compositions are sold as vacuum-dried form that must be reconstituted with a diluent prior to actual usage. One major drawback to using the commercially available *botulinum* toxin preparations is the very short shelf life of the composition. In this regard, the actual usage of the pharmaceutical composition should be administered within about four hours after reconstitution because the *botulinum* toxin is very susceptible to denaturation due to surface denaturation, heat, and alkaline conditions. Further, the patients who has been treated with BoNT needs multiple injections. Some indications of the BoNT product, such as cosmetic use to reduce wrinkles, multiple injections in multiple sites are required. The anesthetics in the composition will reduce the discomfort of the injection. The present invention provides a stable *botulinum* neurotoxin with anesthetic, which has stability up to 150 days. Therefore, the present invention eliminates disadvantage of the currently used vacuum-dried form that must be reconstituted with a diluent prior to actual usage and should be administered within about four hours after reconstitution because the *botulinum* toxin is very susceptible to denaturation due to surface denaturation, heat, and alkaline conditions. These disadvantages of present commercially available BoNTs have been overcome by the formation of the novel composition comprising BoNTs and local anesthetic compound. Local anesthesia is medicine used to numb a small part of your body while you have a procedure or surgery. It is often used during minor surgery or procedures, such as a biopsy or dental care. Lidocaine is one of such commonly used anesthetic. Lidocaine also known as xylocaine or lignocaine is known anesthetic used for nerve block. The present inventors surprisingly found that use of local anesthetic 0.1 to 2% along with *botulinum* neurotoxin preserve or even enhance the activity of *botulinum* neurotoxin up to 150 days at 0 to 8° C. The commonly used anesthetic for preserving the activity of BoNTs are Mepivacaine, bupivacaine (Marcaine), Novocain, Carbocaine (Mepivacaine), Septocaine, Naropin, ropivacaine, Isocaine, Procaine Hydrochloride, chloroprocaine, Xylocaine, articaine (epinephrine) or mixture thereof. The most preferred anesthetic from above is lidocaine.

U.S. Pat. No. 7,744,904 B1 discloses a stable *botulinum* neurotoxin with the help of cyclodextrin. In this cyclodextrin solution the *botulinum* neurotoxin complex has increased stability up to weeks with preservation of up to 80% active *botulinum* neurotoxin species at 4° C. This complex showed up to 56% active neurotoxin over a period of 23 weeks. Whereas present invention provides a stable neurotoxin complex, i.e., up to 80% active neurotoxin at 4° C. over a period of 120 to 150 days. Further, present invention has advantage of using already known anesthetics like lidocaine, which are known active pharmaceutical ingredient.

KR 101135486 discloses liquid phase product of *botulinum* type A toxin along with 2-6 ml of 6-12% dextrose solution and additionally contains anesthetic such as lidocaine, tetracaine, bupivacaine, or dibucaine. The dextrose solution was used in this composition for the stabilization of BoNT.

U.S. Patent Application 20160089440 discloses an extending agent used for dissolving and diluting a *botulinum* toxin type-A product. The potency-extending agent produced by mixing dextrose as a main component, sodium chloride (NaCl) as a first stabilizer, lidocaine as a pain killer, trehalose or sucrose as a second stabilizer, with distilled water for injection.

OBJECTIVE OF THE INVENTION

The main objective of the present invention is to provide a stable pharmaceutical formulation of *botulinum* neurotoxin. Yet another objective of the present invention is use of anesthetic such as lidocaine or other local anesthetic agents as stabilizing agent of *botulinum* neurotoxin in a buffer. Another objective of the present invention is to provide a process for the preparation of stable formulation of *botulinum* neurotoxin with anesthetic such as lidocaine or other local anesthetic agents. Yet another object of the present invention is to provide a method of treatment to reduce wrinkles in human, comprising steps of administrating an effective amount of a pharmaceutical composition of present invention by topical and parenteral administration.

SUMMARY OF THE INVENTION

The present invention seeks to alleviate the problems associated with rapid degradation or denaturation of *botulinum* neurotoxin by providing a novel composition that exhibits improved stability properties. In particular, the present invention seeks to provide a method for producing a *botulinum* neurotoxin composition with improved stability properties in an efficient and economically advantageous manner.

To achieve these and other advantages and in accordance with the purpose of the invention as described herein, the invention includes novel inclusion complexes of *botulinum* neurotoxin which exhibit improved stability properties. The invention also includes method for stabilizing *botulinum* neurotoxin. The neurotoxin is preferably stabilized in the presence of lidocaine in liquid formulation. To replace the lyophilized powder formulations with liquid formulation, there will be no need for reconstitution or the reconstituted formulation will be stable for months at refrigerated temperature. This is a great advantage on the ease of use.

Accordingly the present invention provides a stable composition comprising *botulinum* neurotoxin with the help of anesthetics, more preferably lidocaine. Advantageously, the anesthetic such as lidocaine is present in an amount sufficient to form a complex with the *botulinum* neurotoxin to provide a stabilized *botulinum* neurotoxin. Ordinarily, as known in the art, the *botulinum* neurotoxin is very susceptible to degradation or denaturation. Typically, commercially available *botulinum* neurotoxins, such as BOTOX™, DYSPORT™, and MYOBLOC™ lose their potency in about 4 hours. It has been surprisingly found that in the presence of local anesthetic, *botulinum* neurotoxin complex preserves 80% of the potency of SNAP25 cleavage at least after 4 months at 4° C.

In main embodiment of present invention is to provide a pharmaceutical composition comprising: *botulinum* neurotoxin, anesthetic and a buffer, wherein the anesthetic and the *botulinum* neurotoxin form an association complex.

In another embodiment of the present invention is that the *botulinum* toxin is selected from the group consisting of *botulinum* toxins types A, B, C, D, E, F, G and/or mixture thereof.

In another embodiment of the present invention is that the *botulinum* toxin is type A.

In another embodiment of the present invention is that the *botulinum* neurotoxin is with NAPs or *botulinum* neurotoxin without NAPs or mixture thereof.

In another embodiment of the present invention is that *botulinum* neurotoxin is obtained from *Clostridium botulinum*.

In another embodiment of the present invention is that *botulinum* toxin is purified.

In another embodiment of the present invention is that anesthetic is selected from the group consisting of lidocaine or its derivatives, Mepivacaine, bupivacaine (Marcaine), Novocain, Carbocaine (Mepivacaine), Septocaine, Naropin, ropivacaine, Isocaine, Procaine, chloroprocaine, Xylocaine, articaine (epinephrine) or mixture thereof.

In another embodiment of the present invention is that lidocaine derivative comprises a aminobenzothiazole, diethylamine, N-[(2,6-dimethylphenyl)-carbamoylmethyl-triethylammonium bromide, N,N-bis-(phenylcarbamoylmethyl) dimethylammonium chloride, 4-diethylamino-2,6-butyroxylidide, and/or quaternary amine derivative of lidocaine.

In another embodiment of the present invention is that anesthetic or a derivative thereof is in free form or salt form In another embodiment of the present invention is that lidocaine or derivative thereof is in free form or salt form.

In another embodiment of the present invention is that anesthetic amount in the range of 0.01 to 2% w/v, more preferably in the range of 0.5 to 1% w/v.

In another embodiment of the present invention is that lidocaine or its derivatives amount in the range of 0.01 to 2% w/v, more preferably in the range of 0.5 to 1% w/v.

In another embodiment of the present invention is that buffer is selected from the group consisting of sodium phosphate, potassium phosphate, cacodylate buffer, citrate buffer and mixture thereof.

In another embodiment of the present invention is that buffer is sodium phosphate buffer.

In another embodiment of the present invention is that composition stored at a temperature in the range of 0-8 degree Celsius.

In another embodiment of the present invention is that pH is about 6.8 to about 7.6.

In another embodiment of the present invention is that composition has a shelf life of at least four weeks.

In another embodiment of the present invention is that the *botulinum* neurotoxin in the composition degrades up to 20% over a period of time.

In another embodiment of the present invention is that the period of time for degradation up to 20% of *botulinum* neurotoxin is about 21 weeks.

In another embodiment of the present invention is that ratio of anesthetic to buffer is in the range of 39 to 1

In another embodiment of the present invention is that ratio of anesthetic to sodium phosphate is in the range of 39 to 1

In another embodiment of the present invention is that the ratio of lidocaine to buffer is in the range of 39 to 1.

In another embodiment of the present invention is that the ratio of lidocaine to sodium phosphate is in the range of 39 to 1.

In another embodiment of the present invention is that composition used along with a pharmaceutically acceptable diluent, carrier or excipient, cyclodextrin(s) and/or combination thereof.

In another embodiment of the present invention is that pharmaceutical composition in the form of an injectable solution, or dried preparation.

In another embodiment of the present invention provide a process comprising steps of;
preparing a solution of anesthetic in a buffer
preparing a solution of *botulinum* neurotoxin in a buffer; and
admixing the solution of step a) and step b) to obtain a stable pharmaceutical composition.

In another embodiment of the present invention provide a process, wherein the *botulinum* toxin is selected from the group consisting of *botulinum* toxins types A, B, C, D, E, F, G and/or mixture thereof.

In another embodiment of the present invention provide a process, wherein the *botulinum* toxin is type A.

In another embodiment of the present invention provide a process, wherein the *botulinum* neurotoxin is with NAPs or *botulinum* neurotoxin without NAPs or mixture thereof.

In another embodiment of the present invention provide a process, wherein the *botulinum* neurotoxin is obtained from *Clostridium botulinum*.

In another embodiment of the present invention provide a process, wherein the *botulinum* toxin is purified.

In another embodiment of the present invention is that the anesthetic is selected from the group consisting of lidocaine or its derivatives, Mepivacaine, bupivacaine (Marcaine), Novocain, Carbocaine (Mepivacaine), Septocaine, Naropin, ropivacaine, Isocaine, Procaine Hydrochloride, chloroprocaine, Xylocaine, articaine (epinephrine) or mixture thereof in the process.

In another embodiment of the present invention is that in the process lidocaine derivative used comprises a aminobenzothiazole, diethylamine, N-[(2,6-dimethylphenyl)-carbamoylmethyl-triethylammonium bromide, N,N-bis-(phenylcarbamoylmethyl) dimethylammonium chloride, 4-diethylamino-2,6-butyroxylidide, and/or quaternary amine derivative of lidocaine.

In another embodiment of the present invention is that in process the anesthetic is in free form or salt form In another embodiment of the present invention is that in process the lidocaine or a derivative thereof is in free form or salt form In another embodiment of the present invention is that in process the anesthetic amount in the range of 0.01 to 2% w/v, more preferably in the range of 0.5 to 1% w/v.

In another embodiment of the present invention is that in process the lidocaine or its derivatives amount in the range of 0.01 to 2% w/v, more preferably in the range of 0.5 to 1% w/v. In another embodiment of the present invention is that in process the buffer is selected from the group consisting of sodium phosphate, potassium phosphate, cacodylate buffer, Citrate buffer and mixture thereof.

In another embodiment of the present invention is that in process the pH is about 6.8 to about 7.6.

Yet another embodiment of present invention provides a method for stabilizing *botulinum* neurotoxin, the method comprising:
providing *botulinum* neurotoxin; and subjecting the *botulinum* neurotoxin to an anesthetic in a medium, wherein the anesthetic forms an association complex with the *botulinum* neurotoxin.

Yet another embodiment of present invention provide a method for stabilizing the *botulinum* neurotoxin, wherein the *botulinum* neurotoxin is selected from the group consisting of *botulinum* neurotoxin Type A, B, C, D, E, F and G.

Yet another embodiment of present invention provide a method for stabilizing the *botulinum* neurotoxin, wherein the *botulinum* neurotoxin is *botulinum* neurotoxin Type A.

In another embodiment of the present invention is that in method of stabilizing *botulinum* neurotoxin the anesthetic is selected from the group consisting of lidocaine or its derivatives, Mepivacaine, bupivacaine (Marcaine), Novocain, Carbocaine (Mepivacaine), Septocaine, Naropin, ropivacaine, Isocaine, Procaine Hydrochloride, chloroprocaine, Xylocaine, articaine (epinephrine) or mixture thereof.

In another embodiment of the present invention is that in method of stabilizing *botulinum* neurotoxin, the lidocaine derivative comprises a aminobenzothiazole, diethylamine, N-[(2,6-dimethylphenyl)-carbamoylmethyltriethylammonium bromide, N,N-bis-(phenylcarbamoyl-methyl) dimethylammonium chloride, 4-diethylamino-2,6-butyroxylidide, and/or quaternary amine derivative of lidocaine.

In another embodiment of the present invention is that in method of stabilizing *botulinum* neurotoxin,the anesthetic is in free form or salt form In another embodiment of the present invention is that in method of stabilizing *botulinum* neurotoxin, the lidocaine or a derivative thereof is in free form or salt form In another embodiment of the present invention is that in method of stabilizing *botulinum* neurotoxin, the anesthetic amount in the range of 0.01 to 2% w/v, more preferably in the range of 0.5 to 1% w/v.

In another embodiment of the present invention is that in method of stabilizing *botulinum* neurotoxin, the lidocaine or its derivatives amount in the range of 0.01 to 2% w/v, more preferably in the range of 0.5 to 1% w/v.

Yet another embodiment of present invention provides a method for stabilizing the *botulinum* neurotoxin, wherein the association complex is formed in an aqueous medium.

Yet another embodiment of present invention provides a method for stabilizing the *botulinum* neurotoxin, wherein the aqueous medium has a pH of about 6.8 to 7.6.

Yet another embodiment of present invention provides a method for stabilizing the *botulinum* neurotoxin, wherein pH of the aqueous medium maintained using a buffer.

Yet another embodiment of present invention provides a method for stabilizing *botulinum* neurotoxin, the method comprising:
  providing *botulinum* neurotoxin; and subjecting the *botulinum* neurotoxin to an lidocaine in a medium, wherein the lidocaine forms an association complex with the *botulinum* neurotoxin.

Yet another embodiment of present invention provide a method for stabilizing the *botulinum* neurotoxin, wherein the buffering agent is sodium phosphate, potassium phosphate, cacodylate buffer, Citrate buffer and mixture thereof.

Yet another embodiment of present invention provides a method for stabilizing the *botulinum* neurotoxin, wherein the buffer is of about 10 mM.

Yet another embodiment of present invention provide a method for stabilizing the *botulinum* neurotoxin, wherein the sodium phosphate is of about 10 mM.

Yet another embodiment of present invention provides a method for stabilizing the *botulinum* neurotoxin, wherein the *botulinum* neurotoxin is buffered to have a pH of about 7.4.

Yet another embodiment of present invention provides a method for stabilizing the *botulinum* neurotoxin, wherein stabilizing solution further includes sugars and/or cyclodextrin(s).

Yet another embodiment of present invention provide a method for stabilizing the *botulinum* neurotoxin, wherein about 55% to about 80% of the *botulinum* neurotoxin remains in complex form with the lidocaine for a period of 2 weeks.

Yet another embodiment of present invention provide a method for stabilizing the *botulinum* neurotoxin, wherein the medium for stabilizing *botulinum* neurotoxin comprising lidocaine and sodium phosphate in a ratio of about 39 to 1.

Yet another embodiment of present invention provide a method for stabilizing the *botulinum* neurotoxin, wherein the medium having a pH of about 6.8 to about 7.6.

In another embodiment of present invention provide a method of treatment to reduce wrinkles in human, comprising steps of administrating an effective amount of a pharmaceutical composition comprising anesthetic and *botulinum* neurotoxin in a buffer.

In another embodiment of present invention provide a method of treatment to reduce wrinkles in human with the help of *botulinum* neurotoxin, wherein the *botulinum* neurotoxin is selected from the group consisting of *botulinum* neurotoxin Type A, B, C, D, E, F and G.

In another embodiment of present invention provide a method of treatment to reduce wrinkles in human with the help of *botulinum* neurotoxin composition, wherein the route of administration is topical and parenteral.

In another embodiment of present invention is to provide a method of treatment to reduce wrinkles in human using *botulinum* neurotoxin composition, wherein the *botulinum* neurotoxin is *botulinum* neurotoxin Type A.

In another embodiment of present invention is to provide a method of treatment to reduce wrinkles in human using *botulinum* neurotoxin, wherein the *botulinum* neurotoxin is in an aqueous medium having a pH of about 6.8 to 7.6.

In another embodiment of present invention is to provide a method of treatment to reduce wrinkles in human using *botulinum* neurotoxin, wherein the *botulinum* neurotoxin is in an aqueous medium, wherein pH of the aqueous medium maintained using a buffer.

In another embodiment of present invention is to provide a method of treatment to reduce wrinkles in human using *botulinum* neurotoxin, wherein the *botulinum* neurotoxin is in an aqueous medium comprising a buffer, wherein the buffering agent is sodium phosphate, potassium phosphate, cacodylate buffer, Citrate buffer and mixture thereof.

In another embodiment of present invention is to provide a method of treatment to reduce wrinkles in human using *botulinum* neurotoxin, wherein the *botulinum* neurotoxin is in an aqueous medium comprising a buffer, wherein the buffer is of about 10 mM.

In another embodiment of present invention is to provide a method of treatment to reduce wrinkles in human using *botulinum* neurotoxin, wherein the *botulinum* neurotoxin is in an aqueous medium comprising sodium phosphate, wherein the sodium phosphate of about 10 mM.

In another embodiment of present invention is to provide a method of treatment to reduce wrinkles in human using *botulinum* neurotoxin, wherein the *botulinum* neurotoxin is in an aqueous medium, wherein the *botulinum* neurotoxin is buffered to have a pH of about 7.4.

In another embodiment of present invention is to provide a method of treatment to reduce wrinkles in human using *botulinum* neurotoxin, wherein the *botulinum* neurotoxin is in an aqueous medium, wherein stabilizing solution further comprisess sugars and/or cyclodextrin(s).

In another embodiment of present invention is to provide a method of treatment to reduce wrinkles in human using *botulinum* neurotoxin, wherein the *botulinum* neurotoxin is in an aqueous medium, wherein about 55% to about 80% of the *botulinum* neurotoxin remains in complex form with the anesthetic for a period of 2 weeks.

In another embodiment of present invention is to provide a method of treatment to reduce wrinkles in human using *botulinum* neurotoxin, wherein the *botulinum* neurotoxin is in an aqueous medium, wherein about 55% to about 80% of the *botulinum* neurotoxin remains in complex form with the lidocaine for a period of 2 weeks.

In another embodiment of present invention is to provide a method of treatment to reduce wrinkles in human using *botulinum* neurotoxin, wherein the medium for stabilizing *botulinum* neurotoxin comprising lidocaine and sodium phosphate in a ratio of about 39 to 1.

In another embodiment of present invention is to provide a method of treatment to reduce wrinkles in human using *botulinum* neurotoxin in a medium, wherein the medium having a pH of about 6.8 to about 7.6.

It is to be understood that both the foregoing general description and the following detailed description are exemplary and are intended to provide further explanation of the invention claimed.

DETAILED DESCRIPTION OF THE INVENTION

Figure 1:
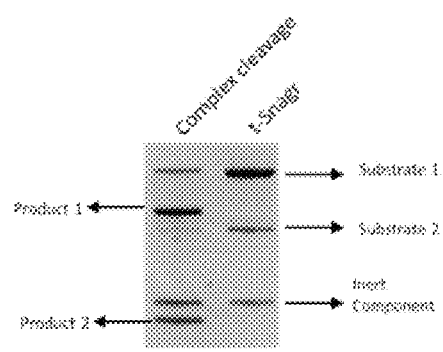
FIG. 1: t-Snagr as the substrate for BoNT/A complex
Figure 2:
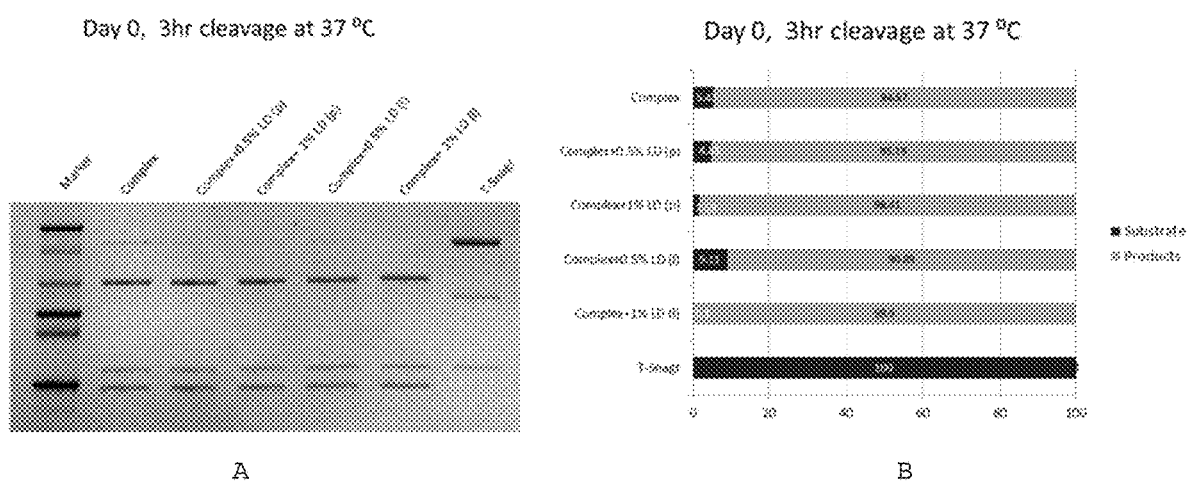
FIG. 2; A & B: The cleavage activity of BoNT/A complex on 0 day analyzed on SDS PAGE gels.
Figure 3:
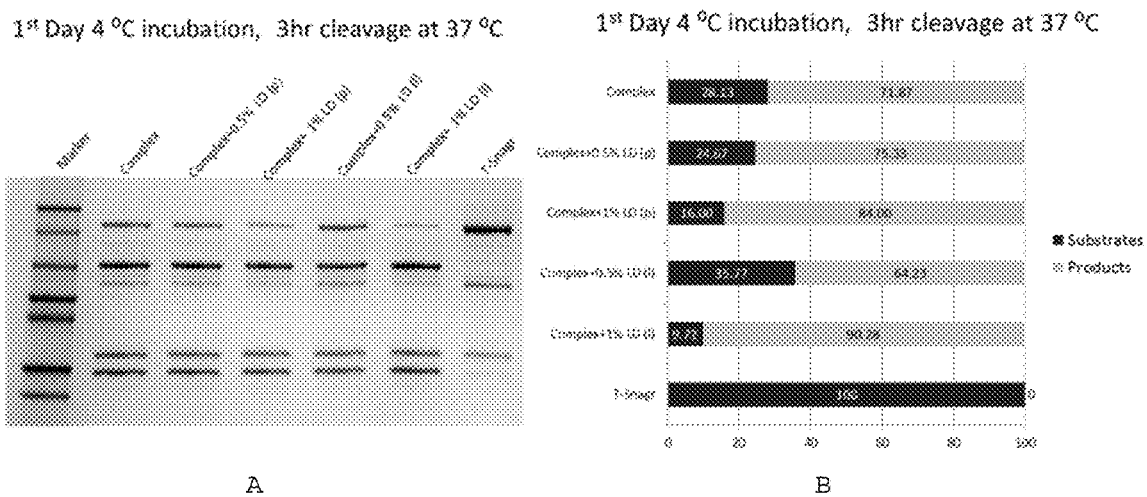
FIG. 3; A & B: The cleavage activity of BoNT/A complex on day 1 analyzed on SDS PAGE gels.
Figure 4:
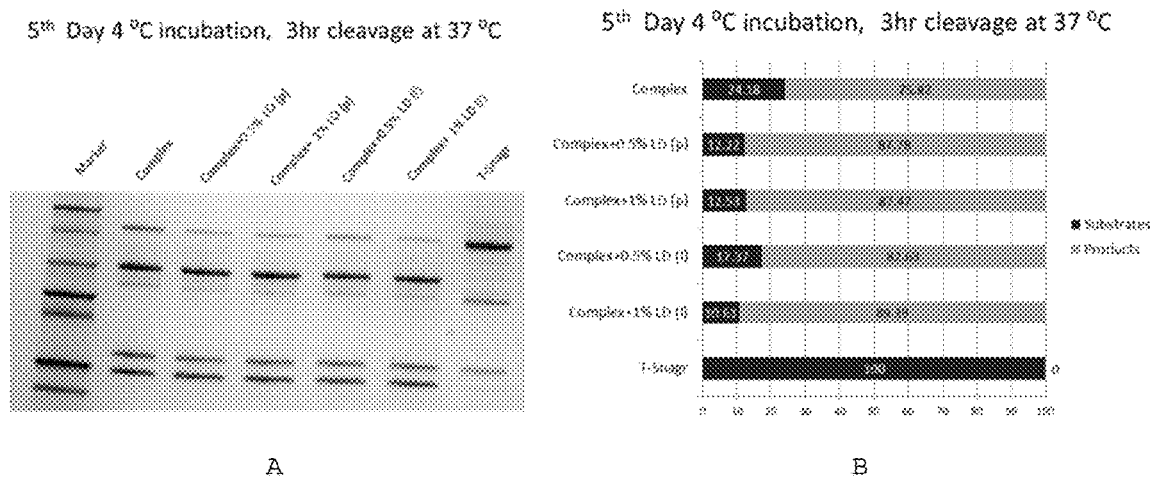
FIG. 4; A & B: The cleavage activity of BoNT/A complex on day 5 analyzed on SDS PAGE gels.
Figure 5:
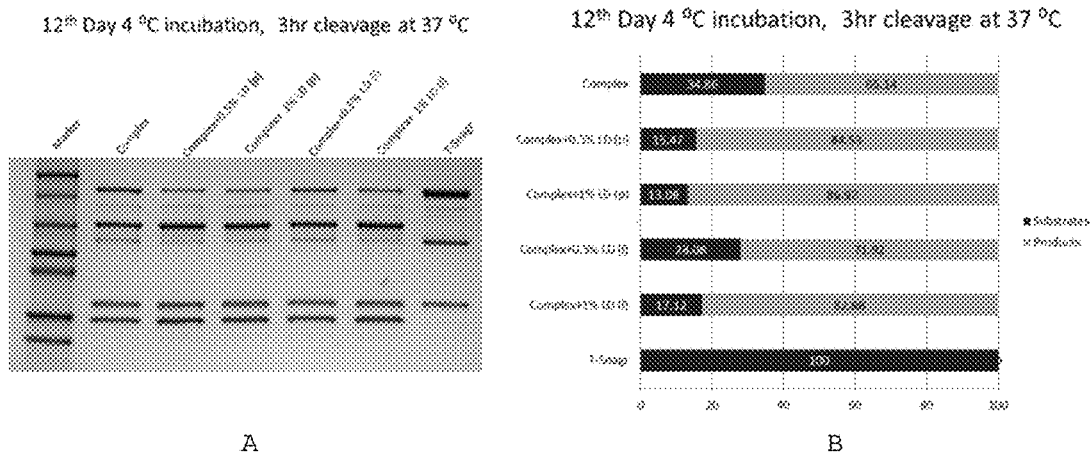
FIG. 5; A & B: The cleavage activity of BoNT/A complex on day 12 analyzed on SDS PAGE gels.
Figure 6:
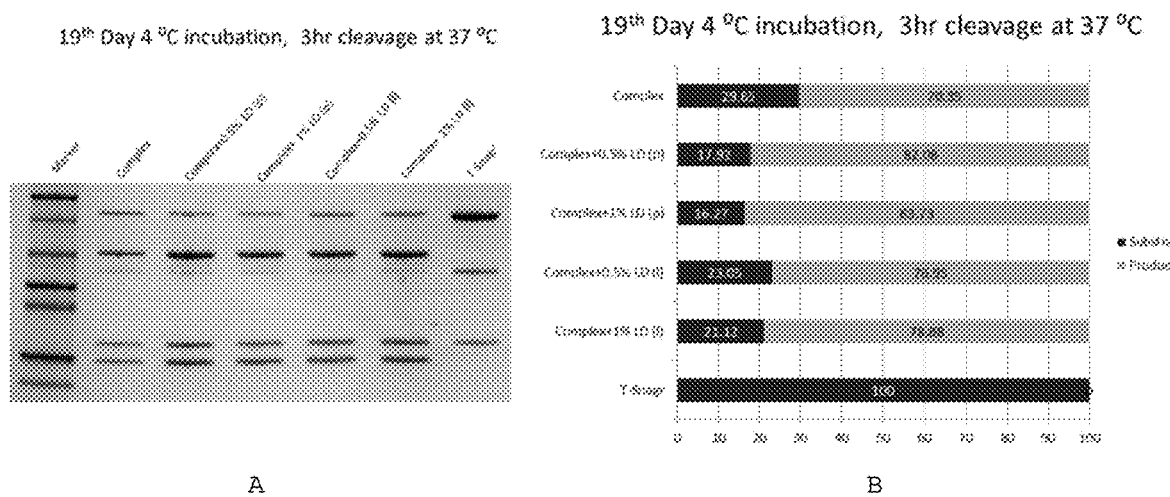
FIG. 6; A & B: The cleavage activity of BoNT/A complex on 19 days analyzed on SDS PAGE gels.
Figure 7:
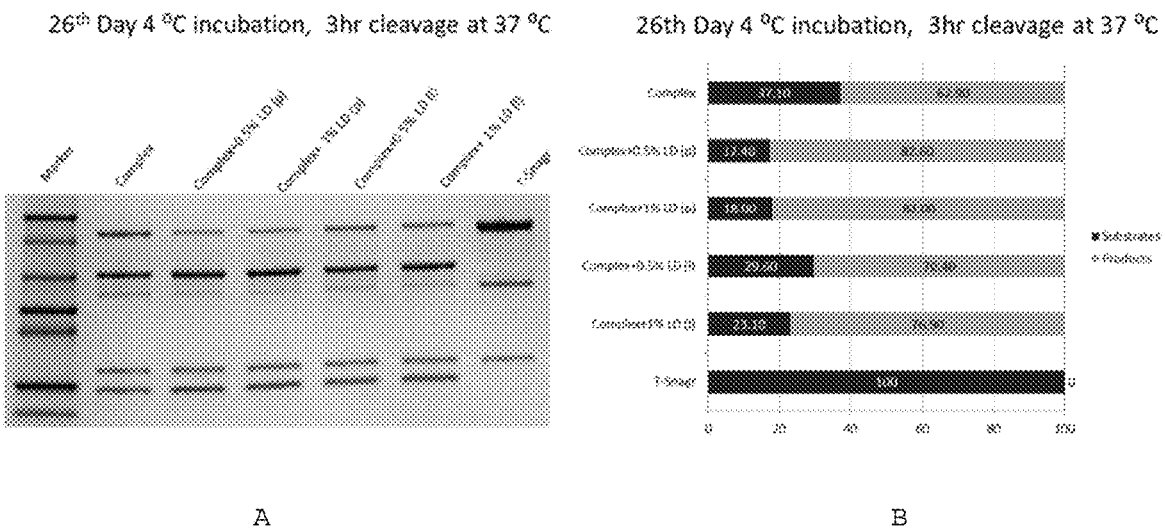
FIG. 7; A & B: The cleavage activity of BoNT/A complex on day 26 analyzed on SDS PAGE gels.
Figure 8:
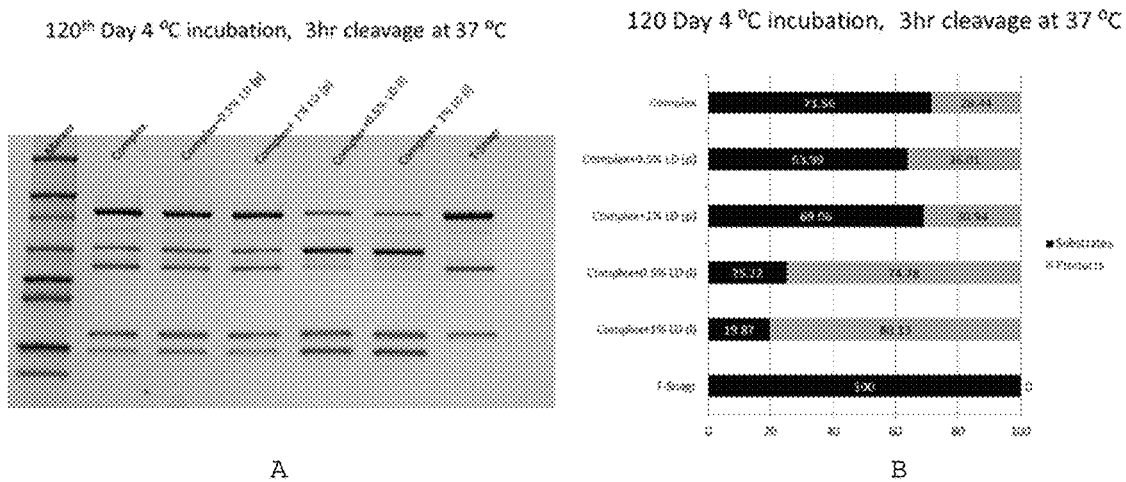
FIG. 8; A & B: The cleavage activity of BoNT/A complex on day 120 analyzed on SDS PAGE gels.
Figure 9:
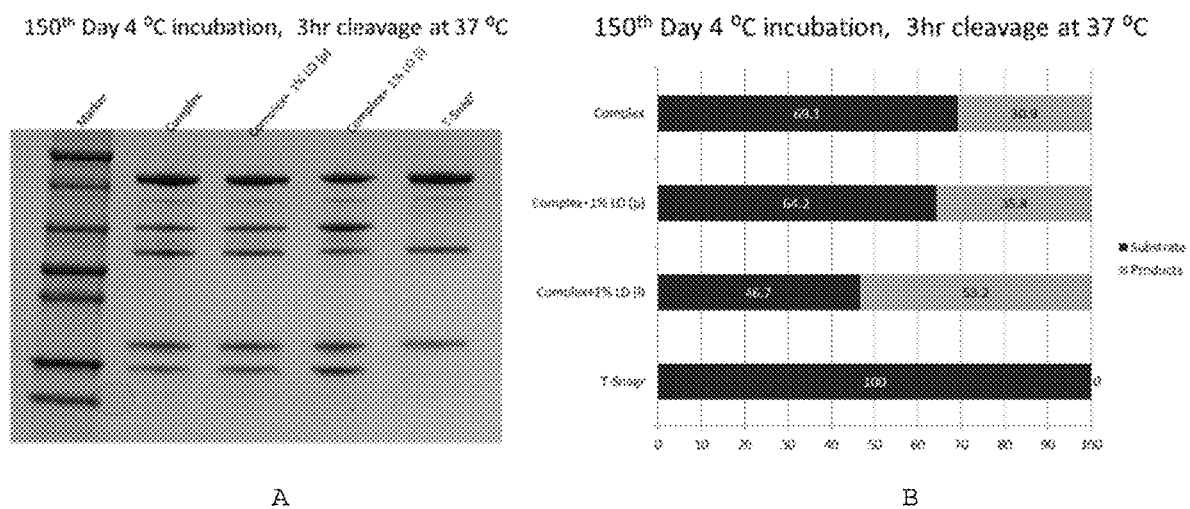
FIG. 9; A & B: The cleavage activity of BoNT/A complex on day 150 analyzed on SDS PAGE gels.

Present invention provides a novel *botulinum* neurotoxin stable for at least four months with the help of anesthetic in a buffer medium. After four months at least 80% of the *botulinum* neurotoxin remains intact in the composition. The composition, for example and not limitation, in the form of an injectable solution, a vacuum dried preparation, or a freeze-dried preparation.

The *botulinum* neurotoxin is selected from A to G and more preferably *botulinum* neurotoxin A. Specifically, and in accordance with the present invention, composition comprises a *botulinum* neurotoxin and anesthetic in a buffer medium, more preferably *botulinum* neurotoxin and lidocaine in a buffer medium. The *botulinum* neurotoxin in the presence of anesthetic exhibits markedly improved stability. More preferably, the composition of *botulinum* neurotoxin used along with lidocaine as an aqueous solution containing a buffer. The amount of anesthetic in the composition can vary from 0.1% to 2%.

The main objective of present invention is to provide a pharmaceutical composition comprising: *botulinum* neurotoxin, anesthetic and a buffer, wherein the anesthetic and the *botulinum* neurotoxin form an association complex. The *botulinum* toxin is selected from the group consisting of *botulinum* toxins types A, B, C, D, E, F, G and/or mixture thereof, more preferably *botulinum* toxin is type A. The *botulinum* neurotoxin is with NAPs or *botulinum* neurotoxin without NAPs or mixture thereof, further it is obained from *Clostridium botulinum* and is purified.

The anesthetic is selected from the group consisting of lidocaine or its derivatives, Mepivacaine, bupivacaine (Marcaine), Novocain, Carbocaine (Mepivacaine), Septocaine, Naropin, ropivacaine, Isocaine, Procaine, chloroprocaine, Xylocaine, articaine (epinephrine) or mixture thereof. Also the lidocaine derivative comprises a aminobenzothiazole, diethylamine, N-[(2,6-dimethylphenyl)-carbamoylmethyl-triethylammonium bromide, N,N-bis-(phenylcarbamoylmethyl) dimethylammonium chloride, 4-diethylamino-2,6-butyroxylidide, and/or quaternary amine derivative of lidocaine. The anesthetic or a derivative thereof used is in free form or salt form, wherein the anesthetic amount in the range of 0.1 to 2% w/v, more preferably in the range of 0.5 to 1% w/v. The buffer is selected from the group consisting of sodium phosphate, potassium phosphate, cacodylate buffer, citrate buffer and mixture thereof.

The composition of present invention is stored at a temperature in the range of 0-8 degree Celsius and the pH is about 6.8 to about 7.6 and has a shelf life of at least four weeks.

The *botulinum* neurotoxin in the composition degrades up to 20% over a period of time and the period of time for degradation up to 20% of *botulinum* neurotoxin is about 21 weeks.

The ratio of anesthetic to buffer is in the range of 39 to 1 wherein the ratio of lidocaine to sodium phosphate is in the range of 39 to 1. Further different composition may use along with a pharmaceutically acceptable diluent, carrier or excipient, cyclodextrin(s) and/or combination thereof.

The composition of present invention is in the form of an injectable solution, or dried preparation.

Present invention provides a process comprising steps of;
preparing a solution of anesthetic in a buffer
preparing a solution of *botulinum* neurotoxin in a buffer; and
admixing the solution of step a) and step b) to obtain a stable pharmaceutical composition.

The present invention also provides a method for stabilizing *botulinum* neurotoxin, the method comprising:
providing *botulinum* neurotoxin; and subjecting the *botulinum* neurotoxin to an lidocaine in a medium, wherein the lidocaine forms an association complex with the *botulinum* neurotoxin.

Present invention further provides a method of treatment to reduce wrinkles in human with the help of *botulinum* neurotoxin composition, wherein the route of administration is topical and parenteral.

Preparation of *C. Botulinum* Type A Neurotoxin

The *C. botulinum* Type A (strain Hall) complex was prepared by the method described in Cai et al. Enhancement of the Endopeptidase Activity of Botulinum Neurotoxin by Its Associated Proteins and Dithiothreitol, Biochemistry, 1999, 38, 6903-6910, the entire contents of which are incorporated herein by reference. The purified Type A complex was subjected to a buffer exchange using a 5 mL Sephadex G-25 column equilibrated with 10 column volumes of 10 mM sodium phosphate, pH 7.4. The Type A complex was determined to have a typical subunit makeup by SDS-PAGE analysis. The Type A complex, at physiological pH of 7.4, was diluted to a 0.75 mg/mL concentration and 1 mL aliquots were placed into eight 1.5 mL microcentrifuge tubes.

Preparation of Botulinum Neurotoxin A-Lidocaine Complex

BoNT/A complex was mixed with two different types of lidocaine: commercially available liquid formulation, which is the same as the first set; and lidocaine powder in citrate buffer pH5.5, which was prepared in our laboratory. BoNT/A complex were mixed with 0.5% or 1% of the two lidocaine solutions and kept at 4° C. for up to 150 days.

The first original lidocaine HCl solution obtained for this study is: 2%, 20 mg/mL in a 50 mL volume. Each mL contains lidocaine hydrochloride anhydrous 20 mg; sodium chloride 6 mg; methylparaben 1 mg added as preservative. May contain HCl and/or NaOH for pH adjustment. pH 6.5 (5.0 to 7.0). Sterile, nonpyrogenic. Store at 20 to 25° C. (68 to 77° F.).

Second type was Lidocaine powder—Lidocaine Hydrochloride Monohydrate (Sigma-Aldrich L5647). Solutions were made with Citrate buffer at pH 5.5. This lidocaine solution was admixed with BoNT/A to form the stable complex. May contain HCl and/or NaOH for pH adjustment. pH 6.5 (5.0 to 7.0). Sterile, nonpyrogenic. Store at 20 to 25° C. (68 to 77° F.).

Testing of Activity of BoNT/A Complex t-Snagr (a derivative of SNAP-25 prepared in our laboratory) was used as the substrate to test the activity of the BoNT/A-lidocane formulation. Citrate Buffer at pH5.5 was used as incubation buffer and PBST buffer at pH 7.4 was used as cleavage buffer. The experimental condition was optimized and BoNT/A complex cleavage activity was close to 100% at the beginning of the study. 4 μM of t-Snagr was incubated with 50 nM BoNT/A Complex after the incubation with different lidocaine solutions. The cleavage was carried out at 37° C. for 3 hrs.

The cleavage activity was determined by the measurement of decrease in Substrate and increase in Product bands. As shown in FIG. 1, the relative density was calculated: Five bands for each cleavage sample. First, we normalized the density by calculate the Ratio of all the bands with the Inert Band; then the Substrate was calculated as the Sum of Substrate bands 1+2, and the Product was calculated as the Sum of Product bands 1+2; The Total was Sum of Substrate and Product. The % Quantity of Sub was the Ratio of Substrate/Total; the % Quantity of Product was the Ratio of Product/Total.

Following complex prepared and studied the cleavage activity at 4° C.

Complex alone (Complex): 50 μl (0.2 mg/mL) (1:4 with citrate buffer)
Lidocaine powder (Complex+LD$_{(p)}$)
Complex +0.5% lidocaine prepared from powder (50 μl), (3:1 complex+citrate to LD)
Complex +1% lidocaine prepared from powder (25 μl), Lidocaine liquid (Complex+LD$_{(l)}$)
Complex +0.5% lidocaine from liquid (50 μl)
Complex +1% lidocaine from commercial liquid (25 μl)
At Day 0, 1, 5, 8, 12, 19, 26, 40, 60, 80, 120, and 150 days, t-SNAGR cleavage was measured 4 μM of t-Snagr was incubated with 50 nM BoNT/A and PBST buffer at pH 7.4 was used as cleavage buffer. The cleavage was carried out in 37° C. for 3 hrs and the cleavage products were run on the SDS PAGE gel.

It is evident from the experiments that in the presence of lidocaine (both powder formula and liquid formula), the cleavage activity of BoNT/A Complex were enhanced compared to Complex alone. Furthermore, 1% lidocaine has more enhanced effect on the cleavage activity of BoNT/A Complex than 0.5% lidocaine.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

I claim:

1. A pharmaceutical composition comprising:
   a *botulinum* neurotoxin, an anesthetic and an aqueous buffer solution, wherein the anesthetic and the *botulinum* neurotoxin form an association complex able to enhance the shelf life of the *botulinum* neurotoxin to at least four weeks;
   wherein the *botulinum* neurotoxin is obtained from a source selected from a group consisting of *Clostridium botulinum, E. coli*, and a plurality of expression systems;
   wherein a pH of the pharmaceutical composition is about 6.8 to about 7.6; and
   wherein a molar ratio of the anesthetic to the aqueous buffer solution in the pharmaceutical composition is 21:1; and,
   wherein the amount of *botulinum* neurotoxin is about 0.10 mg/ml to about 0.15 mg/ml, and the amount of anesthetic is about 0.5% to 1.0% w/v or 0.01 to 2% w/v.

2. The pharmaceutical composition of claim 1, wherein the *botulinum* neurotoxin is selected from the group consisting of *botulinum* toxins Types A, B, C, D, E, F, G and/or mixture thereof.

3. The pharmaceutical composition of claim 2, wherein the *botulinum* neurotoxin is type A.

4. The pharmaceutical composition of claim 1, further comprising a mixture of the *botulinum* neurotoxin with one or more components of neurotoxin-associated proteins (NAPs).

5. The pharmaceutical composition of claim 1, wherein the anesthetic is selected from the group consisting of lidocaine or its derivatives, Mepivacaine, bupivacaine (Marcaine), Novocain, Carbocaine (Mepivacaine), Septocaine, Naropin, ropivacaine, Isocaine, Procaine, chloroprocaine, Xylocaine, articaine (epinephrine), and a mixture thereof.

6. The pharmaceutical composition as claimed in claim 5, wherein the lidocaine derivative comprises a aminobenzothiazole, diethylamine, N[(2, 6-dimethylphenyl)-carbamoyl-methyltriethylammonium bromide, N, N-bis(phenylcarbamoylmethyl) dimethylammonium chloride, 4-diethylamino-2, 6-butyroxylidide, and/or quaternary amine derivative of lidocaine.

7. The pharmaceutical composition as claimed in claim 1, wherein the aqueous buffer solution is selected from a group consisting of sodium phosphate, potassium phosphate, cacodylate buffer, citrate buffer, histidine buffer, and a mixture thereof.

8. The pharmaceutical composition of claim 1, wherein the *botulinum* neurotoxin degrades up to 20% over a time period of 21 weeks.

9. The pharmaceutical composition of claim 1, further comprising a pharmaceutically acceptable diluent, carrier or excipient, cyclodextrin(s) and/or a combination thereof.

10. A process for preparation of a pharmaceutical composition as claimed in claim 1, wherein the process comprises the steps of:
   a) preparing a solution of anesthetic in a buffer;
   b) preparing a solution of *botulinum* neurotoxin in a buffer;
   c) admixing the solution of step a) and step b) to obtain a stable pharmaceutical composition; and
   d) wherein the anesthetic and the *botulinum* neurotoxin form an association complex able to enhance the shelf life of the *botulinum* neurotoxin to at least four weeks;
      wherein the *botulinum* neurotoxin is obtained from a source selected from a group consisting of *Clostridium botulinum, E. coli*, and a plurality of expression systems;
      wherein a pH of the pharmaceutical composition is about 6.8 to about 7.6; and
      wherein a molar ratio of the anesthetic to the aqueous buffer solution in the pharmaceutical composition is 21:1; and,
      wherein the amount of *botulinum* neurotoxin is about 0.10 mg/ml to about 0.15 mg/ml, and the amount of anesthetic is about 0.5% to 1.0% w/v or 0.01 to 2% w/v.

11. The process as claimed in claim 10, wherein the *botulinum* toxin is selected from the group consisting of *botulinum* toxins types A, B, C, D, E, F, G, and a mixture thereof.

12. The process as claimed in claim 10, wherein the *botulinum* toxin is type A, with or without one or more NAPs, or a mixture thereof.

13. The process as claimed in claim 10, wherein the anesthetic is selected from the group consisting of lidocaine or its derivatives, Mepivacaine, bupivacaine (Marcaine), Novocain, Carbocaine (Mepivacaine), Septocaine, Naropin, ropivacaine, Isocaine, Procaine Hydrochloride, chloroprocaine, Xylocaine, articaine (epinephrine), and a mixture thereof.

14. The process as claimed in claim 13, wherein the lidocaine derivative comprises a aminobenzothiazole, diethylamine, N-[(2,6-dimethylphenyl)carbamoylmethyltriethylam monium bromide, N, N-bis-(phenylcarbamoylmethyl) dimethylammonium chloride, 4-diethylamino-2,6-butyroxylidide, and/or quaternary amine derivative of lidocaine.

15. The process as claimed in claim 14, wherein the lidocaine or its derivatives amount are in the range of 0.01 to 2% w/v or 0.5 to 1% w/v.

16. The process as claimed in claim 10, wherein the buffer is selected from the group consisting of sodium phosphate, potassium phosphate, cacodylate buffer, Citrate buffer, histidine, and a mixture thereof, in a pH range of 6.8 to 7.6.

17. The process as claimed in claim 10, wherein stable pharmaceutical composition is used along with a pharmaceutically acceptable diluent, carrier or excipient, cyclodextrin(s) and/or combination thereof.

18. A method for stabilizing *botulinum* neurotoxin, the method comprising:
   a) providing *botulinum* neurotoxin; and subjecting the *botulinum* neurotoxin to anesthetic in a buffer medium, wherein the anesthetic forms an association complex with the *botulinum* neurotoxin;
   b) wherein the anesthetic and the *botulinum* neurotoxin form an association complex able to enhance the shelf life of the *botulinum* neurotoxin to at least four weeks;
      wherein the *botulinum* neurotoxin is obtained from a source selected from a group consisting of *Clostridium botulinum, E. coli*, and a plurality of expression systems;
      wherein a pH of the pharmaceutical composition is about 6.8 to about 7.6;
      wherein a molar ratio of the anesthetic to the aqueous buffer solution in the pharmaceutical composition is 21:1; and,
      wherein the amount of *botulinum* neurotoxin is about 0.10 mg/ml to about 0.15 mg/ml, and the amount of anesthetic is about 0.5% to 1.0% w/v, or 0.01 to 2% w/v.

19. The method as claimed in claim 18, wherein the buffering agent is sodium phosphate, potassium phosphate, cacodylate buffer, Citrate buffer, histidine and/or mixture thereof, at a 10 mM concentration.

20. The method as claimed in claim 18, wherein stabilizing solution further includes sugars and/or cyclodextrin(s).

21. A method of treatment to reduce wrinkles in a human, comprising a step of administrating an effective amount of a pharmaceutical composition claimed in claim 1.

22. The method of treatment as claimed in claim 21, wherein the route of administration is topical and parenteral.

* * * * *